(12) United States Patent
Moon et al.

(10) Patent No.: US 7,084,274 B2
(45) Date of Patent: Aug. 1, 2006

(54) METHOD FOR THE SELECTIVE PREPARATION OF 3-OXO-4-AZA-5α-ANDROSTANE COMPOUND

(75) Inventors: Young-Ho Moon, Suwon-si (KR); Kyung-Ik Lee, Anyang-si (KR); Gha-Seung Park, Yongin-si (KR); Chul-Hyun Park, Seongnam-si (KR); Jae-Cheol Lee, Suwon-si (KR); Gwan-Sun Lee, Seoul (KR); Young-Kil Chang, Seoul (KR)

(73) Assignee: Hanmi Pharm. Co., Ltd., Kyungki-do (KR)

( * ) Notice: Subject to any disclaimer, the term of this patent is extended or adjusted under 35 U.S.C. 154(b) by 0 days.

(21) Appl. No.: 10/524,922

(22) PCT Filed: Aug. 13, 2003

(86) PCT No.: PCT/KR03/01629

§ 371 (c)(1),
(2), (4) Date: Feb. 15, 2005

(87) PCT Pub. No.: WO2004/016595

PCT Pub. Date: Feb. 26, 2004

(65) Prior Publication Data

US 2006/0019979 A1    Jan. 26, 2006

(30) Foreign Application Priority Data

Aug. 19, 2002   (KR) ..................... 10-2002-0048784

(51) Int. Cl.
*C07D 221/18* (2006.01)
*C07D 221/02* (2006.01)

(52) U.S. Cl. .......................................... 546/77; 546/61
(58) Field of Classification Search .................. 546/77, 546/61
See application file for complete search history.

(56) References Cited

U.S. PATENT DOCUMENTS 4,451,576 A    5/1984   Lohr et al.
5,804,576 A    9/1998   Schwartz et al.

FOREIGN PATENT DOCUMENTS

WO    WO 02/46207 A2    6/2002

OTHER PUBLICATIONS

J. Templeton et al., "Zinc-Acetic Acid Reduction of the Steroid 4-En-3-one: Novel Conversion of the 4-En-3-one into the 2-En-4-one via a Vinyl Chloride", *J. Chem. Soc.*, Perkin Trans. 1, vol. 9, 1990, pp. 2581-2584.
P. Xia et al., "Synthesis of N-substituted 3-Oxo-17beta-carboxamide-4-aza-5alpha-androstanes and the Tautomersim of 3-Oxo-4-aza-5-androstenes", *Heterocycles*, vol. 47, No. 2, 1998, pp. 703-716.
W. E. Solomons et al. Synthesis and Antimicrobial properties of 17-beta-amino-4-aza-5alpha-androstane Derivatives. J. Pharm. Sci. vol. 63, No. 1, Jan. 1974, pp. 19-23.

*Primary Examiner*—Charanjit S. Aulakh
(74) *Attorney, Agent, or Firm*—Sughrue Mion, PLLC

(57) ABSTRACT

This invention relates to a method for selectively preparing the 3-oxo-4-aza-5¥á-androstane compound which is used as an intermediate of finasteride by heating 3-oxo-4-aza-5-androstene in a mixture of formic acid and an alkanediol in the presence of zinc.

6 Claims, 2 Drawing Sheets

METHOD FOR THE SELECTIVE PREPARATION OF 3-OXO-4-AZA-5α-ANDROSTANE COMPOUND

FIELD OF THE INVENTION

The present invention relates to an improved method for selectively preparing 3-oxo-4-aza-5α-androstane compound under mild conditions.

DESCRIPTION OF THE PRIOR ART

Finasteride (17β-(N-tert-butylcarbamoyl)-5α-4-aza-androst-1-en-3-on), the compound of formula (II) having an androstane backbone, is effective in treating benign prostatic hypertrophy and androgenetic alopecia:

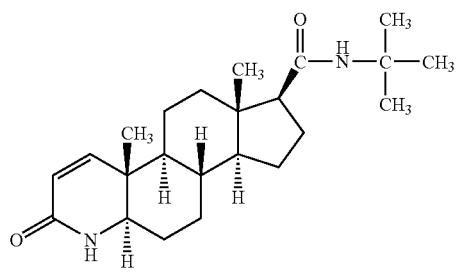

Benign prostatic hypertrophy and androgenetic alopecia are caused by binding of 5α-dihydrotestosterone (DHT) derived from testosterone to androgen receptor. The conversion of testosterone into 5α-dihydrotestosterone is mediated by testosterone 5α-reductase which is inhibited by finasteride. Such inhibition of 5α-dihydrotestosterone by finasteride results in rapid recovery of prostate and increased hair growth. Finasteride thus is effective to benign prostatic hypertrophy and good agent for treating androgenic alopecia which exhibits only low, temporary side effects, and it is the only orally administrable among the two hair-growth agents approved by FDA of the United Sates.

Finasteride can be conventionally prepared by converting the carboxylic group of the 17β-position of 3-oxo-4-aza-5α-androstane-17β-carboxylic acid of formula (I) into a t-butylcarbamoyl group and then carrying out dehydrogenation at the 1,2-positions, or carrying out dehydrogenation at the 1,2-positions and then converting the 17β-position carboxylic group into a t-butylcarbamoyl group:

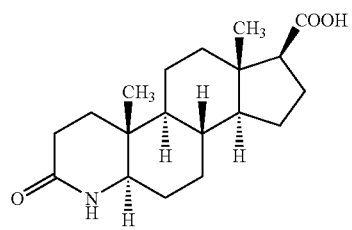

For example, a process for preparing 3-oxo-4-aza-5α-androstane-17β-carboxylic acid of formula (I) is disclosed in U.S. Pat. No. 4,760,071 and the *J. Med. Chem.* 29, 2298 (1986), wherein the 3-oxo-4-aza-5-androstene compound of formula (III) is reduced with the hydrogen in the presence of a $PtO_2$ catalyst under a hydrogen atmosphere of 40 psi to produce the compound of formula (I).

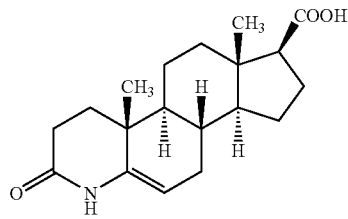

The above reduction process selectively produces the compound of formula (I) having the 5-hydrogen oriented at 5α-position, without giving the isomer thereof, the compound of formula (IV) having the 5-hydrogen at the 5β-position. However, this asymmetric reduction process requires the use of explosive hydrogen and an expensive catalyst under high pressure condition.

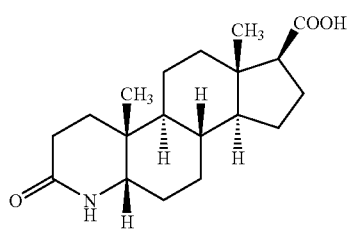

Also disclosed in *J. of Pharmaceutical Sciences.* 63, p 19 (1974) is a method of reducing a steroid compound having a structure similar to the compound of formula (III) to produce a 5α-compound using formic acid and N-methylformamide. However, this process is conducted under high temperature and high pressure conditions and gives a poor productivity.

SUMMARY OF THE INVENTION

Accordingly, it is a primary object of the present invention to provide an improved method for selectively preparing the compound of formula (I) under mild conditions.

In accordance with the present invention, there is provided a method for preparing the compound of formula (I) comprising heating the compound of formula (III) in a mixture of formic acid and an alkanediol in the presence of zinc:

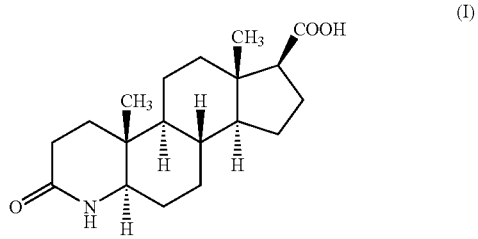

-continued

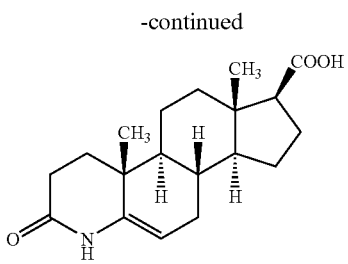

(III)

BRIEF DESCRIPTION OF THE DRAWINGS

The above and other objects and features of the present invention will become apparent from the following description of the invention taken in conjunction with the following accompanying drawings, which respectively show.

DETAILED DESCRIPTION OF THE INVENTION

Figure 1:
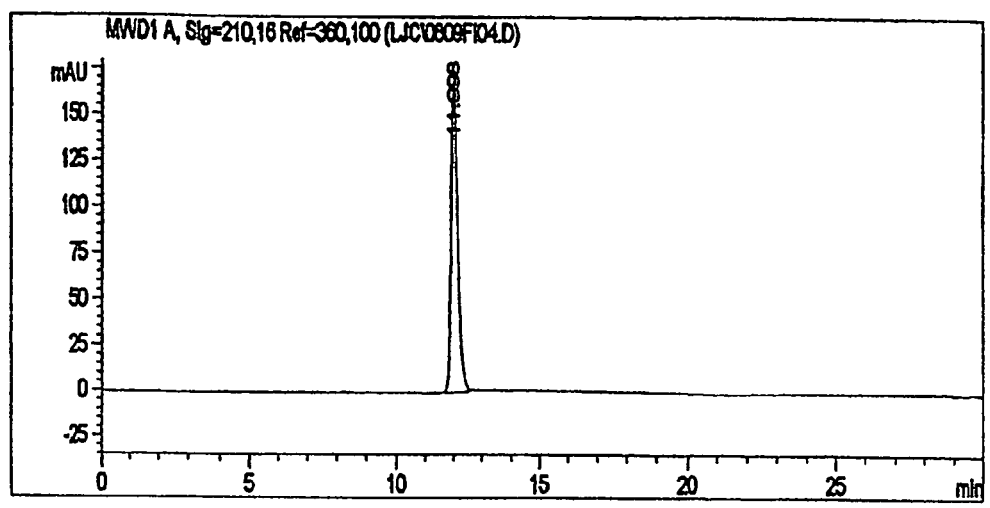
FIG. 1: a high performance liquid chromatography (HPLC) scan of the compound of formula (I) prepared in accordance with the inventive method.

The compound of formula (III) used as a starting material of the present invention can be prepared by a conventional method (U.S. Pat. No. 4,760,071 and the *J. Med. Chem.* 29, 2298 (1986)).

In accordance with the present invention, the compound of formula (I) can be prepared by dissolving the compound of formula (III) in a mixture of formic acid and an alkanediol, adding activated zinc thereto, and heating the resulting mixture.

In the inventive method, formic acid may be used in an amount of 3 to 30 ml, preferably 5 to 15 ml based on 1.0 g of the compound of formula (III); and the alkanediol, in an amount of 2 to 20 ml, preferably 5 to 10 ml, based on 1.0 g of the compound of formula (III).

The alkanediol which may be used in the present invention includes ethylene glycol, propylene glycol, 1,3-propanediol, 1,2-butanediol, 1,3-butanediol, 1,4-butanediol and 2,3-butanediol, and the like, among which ethylene glycol is preferred.

The zinc used in the present invention enhances both the selectivity of the target 5α-compound and the yield, and also reduces the reaction time. Zinc may used in 4 to 10 equivalents, preferably, 6 to 8 equivalents, based on a mole of the compound of formula (III), and in the total absence of the isomeric 5β-byproduct, the target 5α-compound is produced in a high yield of 80%. When zinc is not used, the target 5α-compound is produced in a yield of only about 50% together with 10 to 20% of the isomeric 5β-compound.

The reduction in accordance with the present invention may be carried out at a temperature of 80 to 130° C., preferably 100 to 110° C., for 4 to 8 hours.

Thus, in accordance with the simple method of the present invention, the target compound of formula (I) can be selectively produced in a high yield under mild conditions.

The present invention will be described in further detail with reference to Examples. However, it should be understood that the present is not restricted by the specific Examples.

EXAMPLE

Preparation 1: Preparation of 17β-carboxy-5-oxo-A-nor-3,5-secoandrostan-3-onic acid 16 g (50 mmol) of 3-oxo-4-androstene-17β-carboxylic acid was dissolved in 240 ml of t-butanol, 16 g (150 mmol) of sodium carbonate dissolved in 40 ml of water was added thereto, and then heated to 80° C. Added dropwise thereto was a solution, which is preheated to 60° C., of 53.5 g (250 mmol) of sodium metaperiodate and 4.0 g (25 mmol) of potassium permanganate dissolved in 300 ml of water. The resulting mixture was refluxed for 3 hours and left at room temperature overnight. The inorganic materials were filtered-off through celite, the filtrate was successively washed with water and 250 ml of 10% sodium hydrogen sulfite, t-butanol was removed under a reduced pressure, and the residue was acidified with concentrated HCl. The acidified residue was then extracted with 320 ml of methylene chloride, washed successively with 320 ml of 5% sodium hydrogen sulfite and 320 ml of brine, and distilled under a reduced pressure, to obtain 14.5 g of the title compound (yield: 86%) as a pale yellow solid.

H-NMR($\delta$, CDCl$_3$): 0.82(3H, 19-CH$_3$), 1.16(3H, 18-CH$_3$), 1.20~2.30 (15H, cyclic-CH), 1.53(2H, 1-CH$_2$), 2.40(2H, 2-CH$_2$), 2.50(1H, 17-CH), 11.85(1H, COOH)

Preparation 2: Preparation of 3-oxo-4-aza-5-androstene-17β-carboxylic acid (the Compound of Formula (III))

10 g of 17β-carboxy-5-oxo-A-nor-3,5-secoandrostan-3-onic acid (30 mmol) obtained in Preparation 1 was dissolved in 30 ml of ethylene glycol, and 75 ml of 2.0M ethanolic ammonia solution (150 mmol) was added thereto, stirred for an hour at 40 to 50° C., and refluxed for 12 hours. The resulting mixture was cooled to room temperature and ethanol was distilled off under a reduced pressure. To the residue was added 150 ml of water and the resulting mixture was acidified with 10% HCl to pH 1.5. Precipiates formed were filtered, washed with water, and dried at 45° C., to obtain 6.6 g of the title compound (yield: 70%) as a white solid.

H-NMR($\delta$, DMSO-d$_6$): 0.57(3H, 19-CH$_3$), 0.91(3H, 18-CH$_3$), 0.95~2.30 (18H, cyclic-CH), 4.76(1H, 6-CH), 9.17(1H, NH), 11.85(1H, COOH)

Example 1

3-oxo-4-aza-5α-androstane-17β-carboxylic acid (the Compound of Formula (I)-1)

3.2 g (10 mmol) of 3-oxo-4-aza-5-androstene-17β-carboxylic acid obtained in Preparation 2 was dissolved in a mixture of 45 ml of formic acid and 15 ml of ethylene glycol, and 2.6 g (80 mmol) of activated zinc was added thereto. The mixture was reacted for 8 hours at 100 to 105° C. and cooled to room temperature. The suspended solid was removed by filteration, and the solvent in the filtrate was removed under a reduced pressure. 13 ml of N-methylformamide was added to the residue, and the resulting mixture was stirred for 30 minutes in an ice bath. Precipitates formed were then filtered and dried at 45° C., to obtain 2.6 g of the title compound (yield: 81%) as a white solid.

The product thus obtained was analyzed by HPLC and the result is shown in FIG. 1. As can be seen in FIG. 1, only the target 5α-compound (retention time: 11.996) is detected, the isomeric 5β-compound being not detectable.

H-NMR($\delta$, DMSO-d$_6$): 0.56(3H, 19-CH$_3$), 0.72(3H, 18-CH$_3$), 0.80~1.30 (8H, cyclic-CH), 1.40~1.70(7H, cyclic-CH), 1.87(2H, 16-CH), 2.10(2H, 2-CH$_2$), 2.30(1H, 17-CH), 3.0(1H, 5-CH), 7.15(1H, NH), 11.85(1H, COOH)

Example 2

3-oxo-4-aza-5α-androstane-17β-carboxylic acid (the Compound of Formula (I)-2)

3.2 g (10 mmol) of 3-oxo-4-aza-5-androstene-17β-carboxylic acid obtained in Preparation 2 was dissolved in a mixture of 16 ml of formic acid and 32 ml of ethylene glycol, and 2.6 g (80 mmol) of activated zinc was added thereto. The mixture was reacted for 8 hours at 110 to 120° C., and cooled to room temperature. The suspended solid was removed by filtration, formic acid was removed under a reduced pressure. The residue was dissolved in 300 ml of chloroform and washed successively with 150 ml portions of 5% aqueous sodium carbonate solution (×2) and 150 ml portions of water (×3). The chloroform layer was separated, then dried, filtered and the solvent was removed under a reduced pressure. 13 ml of N-methylformamide was added to the residue and stirred for 30 minutes in an ice bath. Precipitates formed were then filtered and dried at 45° C., to obtain 2.7 g of the title compound (yield: 83%) as a white solid.

The product thus obtained was analyzed by HPLC and the result showed that only the 5α-compound (retention time: 11.996) was produced. H-NMR data was the same as in Example 1.

Comparative Example 1

Preparation of 3-oxo-4-aza-5α-androstane-17β-carboxylic acid (the Compound of Formula (I)) in the Absence of Zinc 3.2 g (10 mmol) of 3-oxo-4-aza-5-androstene-17β-carboxylic acid obtained in Preparation 2 was dissolved in a mixture of 45 ml of formic acid and 15 ml of ethylene glycol, and reacted for 8 hours at 100 to 105° C. The reaction mixture was cooled to room temperature, the residual solid was remove by filtration and the solvent was distilled off under a reduced pressure. 13 ml of N-methylformamide was added to the resulting residue and stirred for 30 minutes in an ice bath. Precipitates formed were then filtered and dried at 45° C., to obtain 1.7 g of the title compound (yield: 53%) as a white solid.

Figure 2:
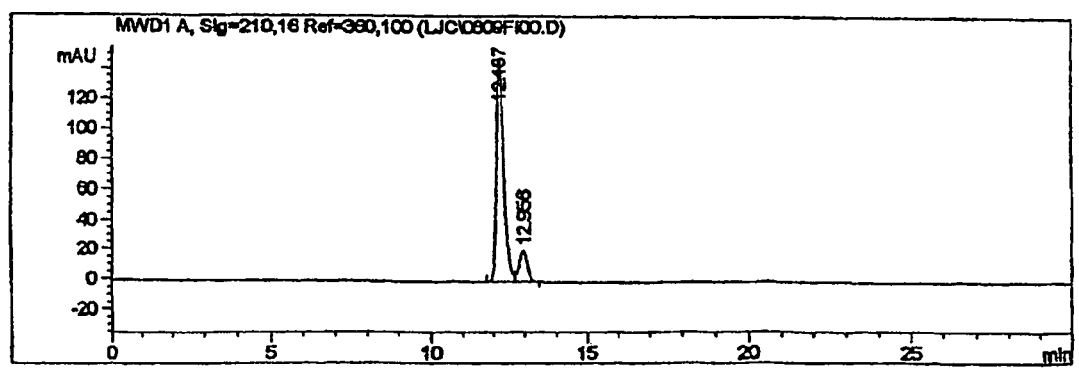
FIG. 2: an HPLC scan of the compound of formula (I) prepared in Comparative Example 1 in the absence of zinc.

The product thus obtained was analyzed by HPLC and the result is shown in FIG. 2, wherein the area of 5β-compound peak (retention time: 12.956) is 15% relative to the area of the 5α-compound peak (retention time: 12.187) of 85%. That is, a large amount of the undesired 5β-compound is produced.

Comparative Example 2

Preparation of 3-oxo-4-aza-5α-androstane-17β-carboxylic acid (the Compound of Formula (I)) Using a Mixture of Formic Acid and N-methylformamide 3.2 g (10 mmol) of 3-oxo-4aza-5-androstene-17β-carboxylic acid obtained in Preparation 2 was dissolved in a mixture of 45 ml of formic acid and 15 ml of N-methylformamide, and reacted for 8 hours at 100 to 105° C. The reaction mixture was cooled to room temperature, the residual solid was filtered off, formic acid was removed under a reduced pressure, and the remaining solution was stirred for 30 minutes in an ice bath. Precipitates formed were then filtered and dried at 45° C., to obtain 1.9 g of the target compound (yield: 59%) as a white solid.

Figure 3:
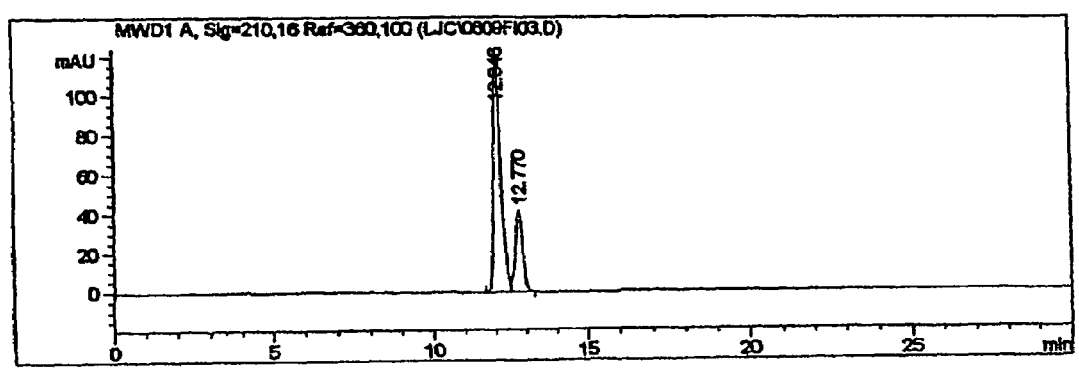
FIG. 3: an HPLC scan of the compound of formula (I) prepared in Comparative Example 2 using formic acid and methylformamide.

The product thus obtained was analyzed by HPLC and the result is shown in FIG. 3, wherein the area of the 5β-compound peak (retention time: 12.770) is 35% relative to the 5α-compound peak (retention time: 12.046) of 65%. That is, a large amount of the undesired 5β-compound is produced.

While the invention has been described with respect to the specific embodiments, it should be recognized that various modifications and changes may be made by those skilled in the art to the invention which also fall within the scope of the invention as defined as the appended claims.

What is claimed is:

1. A method for preparing the compound of formula (I) comprising heating the compound of formula (III) in a mixture of formic acid and an alkanediol in the presence of zinc:

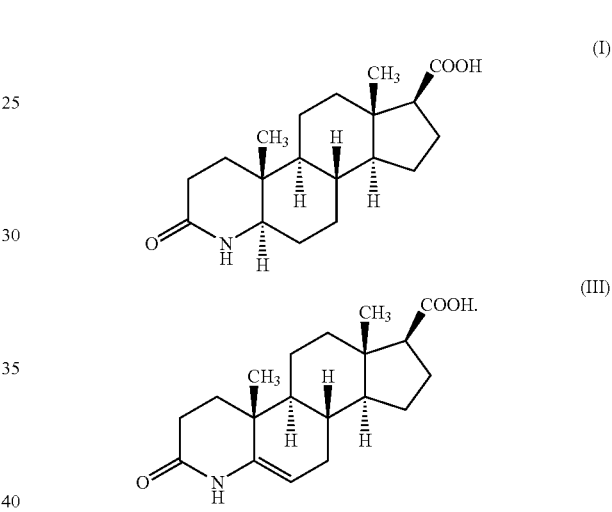

2. The method of claim 1, wherein formic acid is used in an amount of 3 to 30 ml based on 1.0 g of the compound of formula (III).

3. The method of claim 1, wherein the alkanediol is selected from the group consisting of ethylene glycol, propylene glycol, 1,3-propanediol, 1,2-butanediol, 1,3-butanediol, 1,4-butanediol and 2,3-butandiol.

4. The method of claim 1, wherein the alkanediol is used in an amount of 2 to 20 ml based on 1.0 g of the compound of formula (III).

5. The method of claim 1, wherein zinc is used in 4 to 10 equivalents based on a mole of the compound of formula (III).

6. The method of claim 1, wherein the heating is carried out for 4 to 8 hours at a temperature in the range of 80 to 130° C.

* * * * *